United States Patent
Buysse et al.

(10) Patent No.: US 7,137,980 B2
(45) Date of Patent: *Nov. 21, 2006

(54) METHOD AND SYSTEM FOR CONTROLLING OUTPUT OF RF MEDICAL GENERATOR

(75) Inventors: Steven P. Buysse, Longmont, CO (US); Bret S. Felton, Erie, CO (US); David N. Heard, Boulder, CO (US); David Keppel, Longmont, CO (US); Ronald J. Podhajsky, Boulder, CO (US); Dale F. Schmaltz, Fort Collins, CO (US); Robert H. Wham, Boulder, CO (US); Edward C. Meagher, Greenlawn, NY (US); Kate R. Lawes, Superior, CO (US); David A. Schechter, Longmont, CO (US); Chelsea Shields, Boulder, CO (US); Philip M. Tetzlaff, Superior, CO (US)

(73) Assignee: Sherwood Services AG, Schaffhausen (CH)

( * ) Notice: Subject to any disclaimer, the term of this patent is extended or adjusted under 35 U.S.C. 154(b) by 250 days.

This patent is subject to a terminal disclaimer.

(21) Appl. No.: 10/427,832

(22) Filed: May 1, 2003

(65) Prior Publication Data

US 2004/0015163 A1    Jan. 22, 2004

Related U.S. Application Data (63) Continuation-in-part of application No. 10/073,761, filed on Feb. 11, 2002, now Pat. No. 6,796,981, which is a continuation-in-part of application No. 09/408,944, filed on Sep. 30, 1999, now Pat. No. 6,398,779.

(60) Provisional application No. 60/105,417, filed on Oct. 23, 1998.

(51) Int. Cl.
   *A61B 18/18* (2006.01)
(52) U.S. Cl. .................................. 606/34; 606/42
(58) Field of Classification Search ............ 606/32–34, 606/37–42

See application file for complete search history.

(56) References Cited

U.S. PATENT DOCUMENTS

| | | | |
|---|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 2,982,881 A | 5/1961 | Reich |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,662,151 A | 5/1972 | Haffey |
| 3,675,655 A | 7/1972 | Sittner |
| 3,683,923 A | 8/1972 | Anderson |

| | | |
|---|---|---|
| 3,693,613 A | 9/1972 | Charles Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oostein |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,437,464 A | 3/1984 | Crow |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,590,934 A | 5/1986 | Malis et al. |
| 4,608,977 A | 9/1986 | Brown |
| 4,630,218 A | 12/1986 | Hurley |
| 4,632,109 A | 12/1986 | Patterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,712,559 A | 12/1987 | Turner |
| 5,720,744 A | 2/1988 | Eggleston et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,805,621 A | 2/1989 | Heinze et al. |
| 4,818,954 A | 4/1989 | Flachenecker et al. |
| 4,827,911 A | 5/1989 | Broadwin et al. |
| 4,827,927 A | 5/1989 | Newton |
| 4,832,024 A | 5/1989 | Boussignac et al. |
| 4,848,335 A | 7/1989 | Manes |
| 4,848,355 A | 7/1989 | Nakamura et al. |
| 4,860,745 A | 8/1989 | Farin et al. |
| 4,862,889 A | 9/1989 | Feucht |
| 4,880,719 A | 11/1989 | Murofushi et al. |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,961,047 A | 10/1990 | Carder |
| 4,961,435 A | 10/1990 | Kitagawa et al. |
| 4,966,597 A | 10/1990 | Cosman |
| RE33,420 E | 11/1990 | Sussman |
| 4,969,885 A | 11/1990 | Farin |
| 4,993,430 A | 2/1991 | Shimoyama et al. |
| 4,995,877 A | 2/1991 | Ams et al. |
| 5,015,227 A | 5/1991 | Broadwin et al. |
| 5,019,176 A | 5/1991 | Brandhorst, Jr. |
| 5,029,588 A | 7/1991 | Yock et al. |
| 5,087,257 A | 2/1992 | Farin |
| 5,103,804 A | 4/1992 | Abele et al. |
| 5,108,389 A | 4/1992 | Cosmescu |
| 5,108,391 A | 4/1992 | Flachenecker |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |

| | | |
|---|---|---|
| 5,157,603 A | 10/1992 | Scheller et al. |
| 5,160,334 A | 11/1992 | Billings et al. |
| 5,162,217 A | 11/1992 | Hartman |
| 5,167,658 A | 12/1992 | Ensslin |
| 5,190,517 A | 3/1993 | Zieve et al. |
| 5,196,008 A | 3/1993 | Kuenecke |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,267,994 A | 12/1993 | Gentelia et al. |
| 5,267,997 A | 12/1993 | Farin |
| 5,281,213 A | 1/1994 | Milder et al. |
| 5,300,068 A | 4/1994 | Rosar et al. |
| 5,300,070 A | 4/1994 | Gentelia |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,193 A | 8/1994 | Nardella |
| 5,341,807 A * | 8/1994 | Nardella ............ 600/381 |
| 5,342,356 A | 8/1994 | Ellman et al. |
| 5,342,357 A | 8/1994 | Nardella |
| 5,342,409 A | 8/1994 | Mullett |
| 5,348,554 A | 9/1994 | Imran et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson |
| 5,383,876 A | 1/1995 | Nardella |
| 5,383,917 A | 1/1995 | Desai et al. |
| 5,385,148 A | 1/1995 | Lesh et al. |
| 5,396,062 A | 3/1995 | Eisentraut et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,006 A | 4/1995 | Buchholtz et al. |
| 5,409,485 A | 4/1995 | Suda |
| 5,413,573 A | 5/1995 | Koivukangas |
| 5,417,719 A | 5/1995 | Hull et al. |
| 5,422,567 A | 6/1995 | Matsunaga |
| 5,423,808 A | 6/1995 | Edwards et al. |
| 5,423,809 A | 6/1995 | Klicek |
| 5,423,810 A | 6/1995 | Goble et al. |
| 5,430,434 A | 7/1995 | Lederer et al. |
| 5,432,459 A | 7/1995 | Thompson |
| 5,433,739 A | 7/1995 | Sluijter et al. |
| 5,434,398 A | 7/1995 | Goldberg |
| 5,436,566 A | 7/1995 | Thompson |
| 5,438,302 A | 8/1995 | Goble |
| 5,443,463 A | 8/1995 | Stern et al. |
| 5,445,635 A | 8/1995 | Denen |
| 5,451,224 A | 9/1995 | Goble et al. |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,478,303 A | 12/1995 | Foley-Nolan et al. |
| 5,480,399 A | 1/1996 | Hebborn |
| 5,483,952 A | 1/1996 | Aranyi |
| 5,490,850 A | 2/1996 | Ellman et al. |
| 5,496,312 A | 3/1996 | Klicek |
| 5,496,313 A | 3/1996 | Gentelia et al. |
| 5,500,012 A | 3/1996 | Brucker et al. |
| 5,500,616 A | 3/1996 | Ochi |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,681 A * | 7/1996 | Strul et al. ............ 606/34 |
| 5,540,683 A | 7/1996 | Ichikawa |
| 5,540,684 A | 7/1996 | Hassler, Jr. |
| 5,540,724 A | 7/1996 | Cox |
| 5,556,396 A | 9/1996 | Cohen et al. |
| 5,558,671 A * | 9/1996 | Yates ............ 606/38 |
| 5,569,242 A | 10/1996 | Lax et al. |
| 5,571,147 A | 11/1996 | Sluijter et al. |
| 5,573,533 A | 11/1996 | Strul |
| 5,588,432 A | 12/1996 | Crowley |
| 5,594,636 A | 1/1997 | Schauder |
| 5,596,466 A | 1/1997 | Ochi |
| 5,599,344 A | 2/1997 | Paterson |
| 5,599,345 A | 2/1997 | Edwards et al. |
| 5,605,150 A | 2/1997 | Radons et al. |
| 5,613,966 A | 3/1997 | Makower et al. |
| 5,613,996 A | 3/1997 | Lindsay |
| 5,625,370 A | 4/1997 | D'Hont |
| 5,626,575 A | 5/1997 | Crenner |
| 5,628,745 A | 5/1997 | Bek |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,688,267 A * | 11/1997 | Panescu et al. ............ 606/41 |
| 5,690,692 A | 11/1997 | Fleming |
| 5,693,042 A | 12/1997 | Bioarski et al. |
| 5,695,494 A | 12/1997 | Becker |
| 5,696,351 A | 12/1997 | Benn et al. |
| 5,702,386 A | 12/1997 | Stern et al. |
| 5,702,429 A | 12/1997 | King |
| 5,707,369 A | 1/1998 | Vaitekunas et al. |
| 5,713,896 A | 2/1998 | Nardella |
| 5,722,975 A | 3/1998 | Edwards et al. |
| 5,733,281 A | 3/1998 | Nardella |
| 5,749,869 A | 5/1998 | Lindenmeir et al. |
| 5,749,871 A | 5/1998 | Hood et al. |
| 5,755,715 A | 5/1998 | Stern |
| 5,766,165 A | 6/1998 | Gentelia et al. |
| 5,769,847 A | 6/1998 | Panescu |
| 5,772,659 A | 6/1998 | Becker et al. |
| 5,792,138 A | 8/1998 | Shipp |
| 5,797,802 A | 8/1998 | Nowak |
| 5,797,902 A | 8/1998 | Netherly |
| 5,814,092 A | 9/1998 | King |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell |
| 5,836,943 A | 11/1998 | Miller, III |
| 5,836,990 A | 11/1998 | Li |
| 5,846,236 A | 12/1998 | Lindenmeier et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,893,848 A * | 4/1999 | Negus et al. ............ 606/41 |
| 5,897,552 A | 4/1999 | Edwards et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,938,690 A | 8/1999 | Law et al. |
| 5,948,007 A | 9/1999 | Starkebaum et al. |
| 5,951,545 A | 9/1999 | Schilling |
| 5,951,546 A | 9/1999 | Lorentzen |
| 5,954,686 A | 9/1999 | Garito et al. |
| 5,954,717 A | 9/1999 | Behl et al. |
| 5,961,344 A | 10/1999 | Rosales et al. |
| 5,971,980 A | 10/1999 | Sherman |

| | | | | | |
|---|---|---|---|---|---|
| 5,976,128 A | 11/1999 | Schilling et al. | 6,648,883 B1 | 11/2003 | Francischelli |
| 5,983,141 A | 11/1999 | Sluijter et al. | 6,652,514 B1 | 11/2003 | Ellman |
| 6,010,499 A | 1/2000 | Cobb | 6,663,623 B1 | 12/2003 | Oyama et al. |
| 6,014,581 A | 1/2000 | Whayne et al. | 6,663,624 B1 | 12/2003 | Edwards |
| 6,033,399 A | 3/2000 | Gines | 6,666,860 B1 | 12/2003 | Takahashi |
| 6,044,283 A | 3/2000 | Fein et al. | 6,679,875 B1 | 1/2004 | Honda |
| 6,053,910 A | 4/2000 | Fleenor | 6,682,527 B1 | 1/2004 | Strul |
| 6,053,912 A | 4/2000 | Panescu et al. | 6,685,700 B1 | 2/2004 | Behl |
| 6,056,745 A | 5/2000 | Panescu et al. | 6,685,701 B1 | 2/2004 | Orszulak et al. |
| 6,056,746 A | 5/2000 | Goble et al. | 6,692,489 B1 | 2/2004 | Heim |
| 6,063,075 A | 5/2000 | Mihori | 6,712,813 B1 | 3/2004 | Ellman |
| 6,063,078 A | 5/2000 | Wittkampf | 6,730,080 B1 | 5/2004 | Harano |
| 6,068,627 A | 5/2000 | Orszulak et al. | 6,733,495 B1 | 5/2004 | Bek |
| 6,074,386 A | 6/2000 | Goble et al. | 6,733,498 B1 | 5/2004 | Paton |
| 6,080,149 A | 6/2000 | Huang et al. | 6,740,079 B1 | 5/2004 | Eggers |
| 6,093,186 A | 7/2000 | Goble | 6,740,085 B1 | 5/2004 | Hareyama |
| RE36,871 E | 9/2000 | Epstein | 6,783,523 B1 | 8/2004 | Qin |
| 6,113,591 A | 9/2000 | Whayne et al. | 6,790,206 B1 | 9/2004 | Panescu |
| 6,113,596 A | 9/2000 | Hooven | 6,796,981 B1 * | 9/2004 | Wham et al. ............... 606/34 |
| 6,123,702 A | 9/2000 | Swanson et al. | 6,824,539 B1 | 11/2004 | Novak |
| 6,132,429 A | 10/2000 | Baker | 6,830,569 B1 | 12/2004 | Thompson |
| 6,142,992 A | 11/2000 | Cheng et al. | 6,843,789 B1 | 1/2005 | Goble |
| 6,162,217 A | 12/2000 | Kannenberg et al. | 6,849,073 B1 | 2/2005 | Hoey |
| 6,203,541 B1 | 3/2001 | Keppel | 6,855,141 B1 | 2/2005 | Lovewell |
| 6,210,403 B1 | 4/2001 | Klicek | 6,855,142 B1 | 2/2005 | Harano |
| 6,228,080 B1 | 5/2001 | Gines | 6,860,881 B1 | 3/2005 | Sturm |
| 6,228,081 B1 | 5/2001 | Goble | 6,864,686 B1 | 3/2005 | Novak |
| 6,231,569 B1 | 5/2001 | Bek | 6,875,210 B1 | 4/2005 | Refior |
| 6,235,020 B1 | 5/2001 | Cheng et al. | 6,893,435 B1 | 5/2005 | Goble |
| 6,238,387 B1 | 5/2001 | Miller, III | 2001/0014804 A1 | 8/2001 | Goble et al. |
| 6,238,388 B1 | 5/2001 | Ellman | 2001/0031962 A1 | 10/2001 | Eggleston |
| 6,241,725 B1 | 6/2001 | Cosman | 2002/0035353 A1 | 3/2002 | Edwards et al. |
| 6,245,065 B1 | 6/2001 | Panescu | 2002/0035363 A1 | 3/2002 | Edwards et al. |
| 6,246,912 B1 | 6/2001 | Sluijter et al. | 2002/0035364 A1 | 3/2002 | Schoenman et al. |
| 6,251,106 B1 | 6/2001 | Becker et al. | 2002/0068932 A1 | 6/2002 | Edwards |
| 6,258,085 B1 | 7/2001 | Eggleston | 2002/0193787 A1 | 12/2002 | Qin |
| 6,261,285 B1 | 7/2001 | Novak | 2003/0004510 A1 | 1/2003 | Wham et al. |
| 6,273,886 B1 | 8/2001 | Edwards | 2003/0060818 A1 | 3/2003 | Kannenberg |
| 6,275,786 B1 | 8/2001 | Daners | 2003/0078572 A1 | 4/2003 | Pearson et al. |
| 6,293,941 B1 | 9/2001 | Strul | 2003/0139741 A1 | 7/2003 | Goble et al. |
| 6,293,942 B1 | 9/2001 | Goble et al. | 2003/0153908 A1 | 8/2003 | Goble |
| 6,306,131 B1 | 10/2001 | Hareyama et al. | 2003/0163123 A1 | 8/2003 | Goble |
| 6,306,134 B1 | 10/2001 | Goble et al. | 2003/0163124 A1 | 8/2003 | Goble |
| 6,309,386 B1 | 10/2001 | Bek | 2003/0171745 A1 | 9/2003 | Francischelli |
| 6,337,998 B1 | 1/2002 | Behl et al. | 2003/0199863 A1 | 10/2003 | Swanson |
| 6,338,657 B1 | 1/2002 | Harper et al. | 2004/0002745 A1 | 1/2004 | Flemming |
| 6,358,245 B1 | 3/2002 | Edwards | 2004/0019347 A1 | 1/2004 | Sakurai |
| 6,383,183 B1 | 5/2002 | Sekino et al. | 2004/0024395 A1 | 2/2004 | Ellman |
| 6,398,779 B1 * | 6/2002 | Buysse et al. ............... 606/34 | 2004/0030328 A1 | 2/2004 | Eggers |
| 6,398,781 B1 | 6/2002 | Goble et al. | 2004/0044339 A1 | 3/2004 | Beller |
| 6,402,741 B1 | 6/2002 | Keppel et al. | 2004/0049179 A1 | 3/2004 | Francischelli |
| 6,402,743 B1 | 6/2002 | Orszulak et al. | 2004/0054365 A1 | 3/2004 | Goble |
| 6,416,509 B1 | 7/2002 | Goble et al. | 2004/0068304 A1 | 4/2004 | Paton |
| 6,436,096 B1 | 8/2002 | Hareyama | 2004/0082946 A1 | 4/2004 | Malis |
| 6,451,015 B1 | 9/2002 | Rittman, III et al. | 2004/0097912 A1 | 5/2004 | Gonnering |
| 6,458,121 B1 | 10/2002 | Rosenstock | 2004/0097914 A1 | 5/2004 | Pantera |
| 6,464,689 B1 | 10/2002 | Qin | 2004/0097915 A1 | 5/2004 | Refior |
| 6,464,696 B1 | 10/2002 | Oyama | 2004/0116919 A1 | 6/2004 | Heim |
| 6,506,189 B1 | 1/2003 | Rittman, III et al. | 2004/0133189 A1 | 7/2004 | Sakurai |
| 6,508,815 B1 | 1/2003 | Strul | 2004/0138653 A1 | 7/2004 | Dabney |
| 6,511,476 B1 | 1/2003 | Hareyama | 2004/0138654 A1 | 7/2004 | Goble |
| 6,364,877 B1 | 4/2003 | Goble et al. | 2004/0172016 A1 | 9/2004 | Bek |
| 6,547,786 B1 | 4/2003 | Goble | 2004/0193148 A1 * | 9/2004 | Wham et al. ............... 606/40 |
| 6,558,376 B1 | 5/2003 | Bishop | 2004/0230189 A1 | 11/2004 | Keppel |
| 6,562,037 B1 | 5/2003 | Paton | 2004/0243120 A1 | 12/2004 | Orszulak et al. |
| 6,565,559 B1 | 5/2003 | Eggleston | 2004/0260279 A1 | 12/2004 | Goble |
| 6,573,248 B1 | 6/2003 | Ramasamy et al. | 2005/0004564 A1 | 1/2005 | Wham |
| 6,575,969 B1 | 6/2003 | Rittman, III et al. | 2005/0021022 A1 | 1/2005 | Sturm et al. |
| 6,582,427 B1 | 6/2003 | Goble et al. | 2005/0101951 A1 | 5/2005 | Wham |
| 6,261,286 B1 | 7/2003 | Goble et al. | 2005/0113818 A1 | 5/2005 | Sartor |
| 6,620,157 B1 | 9/2003 | Dabney et al. | 2005/0113819 A1 | 5/2005 | Wham |
| 6,623,423 B1 | 9/2003 | Sakurai | 2005/0149151 A1 | 7/2005 | Orszulak |
| 6,635,056 B1 * | 10/2003 | Kadhiresan et al. ......... 606/34 | 2005/0182398 A1 | 8/2005 | Paterson |

| | | | | | | |
|---|---|---|---|---|---|---|
| 2005/0197659 | A1 | 9/2005 | Bahney | WO | WO02/045589 | 6/2002 |
| 2005/0203504 | A1 | 9/2005 | Wham et al. | WO | WO02/47565 | 6/2002 |
| 2006/0025760 | A1 | 2/2006 | Podhajsky | WO | WO02/088128 | 7/2002 |

FOREIGN PATENT DOCUMENTS

| | | |
|---|---|---|
| DE | 179607 | 3/1905 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2607517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 19717411 A1 | 4/1997 |
| DE | 19717411 | 11/1998 |
| DE | 19717411 A1 | 11/1998 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 878169 | 11/1998 |
| EP | 1293171 | 3/2003 |
| FR | 1275415 | 10/1961 |
| FR | 1347865 | 11/1963 |
| FR | 2517953 | 6/1973 |
| FR | 2313708 | 12/1976 |
| FR | 2502935 | 10/1982 |
| FR | 2517853 | 6/1983 |
| FR | 2573301 | 5/1986 |
| GB | 607850 | 9/1948 |
| GB | 855459 | 11/1960 |
| GB | 902775 | 8/1962 |
| GB | 2164473 | 3/1986 |
| GB | 2214430 | 9/1989 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39914 | 12/1996 |
| WO | WO96/06740 | 2/1997 |
| WO | WO97/06739 | 2/1997 |
| WO | WO97/06855 | 2/1997 |
| WO | WO97/17029 | 5/1997 |
| WO | WO02/011634 | 2/2002 |

OTHER PUBLICATIONS

Vallfors and Bergdahl, "Automatically Controlled Bipolar Electrocoagulation" Neurosurgical Review, 7:2-3, pp. 187-190. 1984.

Bergdahl and Vallors "Studies on Coagulation and the Development of an Automatic Computerized Bipolar Coagulator" Journal of Neurosurgery, 75:1, 148 151, Jul. 1991.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Anderson et al., "A Numerical Study of Rapid Heating for High Temperature Radio Frequency Hyperthermia" International Journal of Bio-Medical Computing, 35 (1994) pp. 297-307.

Astrahan, "A Localized Current Field Hyperthermia System for Use with 192-Iridium Interstitial Implants"Medical Physics, 9 (3), May/Jun. 1982.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and Its Effect on Tissue Impedance" Applied Neurophysiology 51: (1988) pp. 230-242.

Cosman et al., "Theoretical Aspects of Radiofrequency Lesions in the Dorsal Root Entry Zone" Neurosurgery 15: (1984) pp. 945-950.

Geddes et al., "The Measurement of Physiologic Events by Electrical Impedence" Am. J. MI, Jan. Mar. 1964, pp. 16-27.

Goldberg et al., "Tissue Ablation with Radiofrequency: Effect of Probe Size, Gauge, Duration, and Temperature on Lesion Volume".

Sugita et al., "Bipolar Coagulator with Automatic Thermocontrol" J. Neurosurg., vol. 41, Dec. 1944, pp. 777-779.

Wald et al., "Accidental Burns", JAMA, Aug. 16, 1971, vol. 217, No. 7, pp. 916-921.

Ogden "Goertzel Alternative to the Fourier Transform" Jun. 1993 pp. 485-487 Electronics World; Reed Business Publishing, Sutton, Surrey, GB vol. 99, No. 1687.

International Search Report—PCT/US03/37310.
EP Search Report 4009964.
International Search Report—PCT/US03/37110.
International Search Report—PCT/US03/37310.
International Search Report—EP4009964.
International Search Report—EP98300964.8.
International Search Report—EP04015981.6.

Chicharo et al. "A Sliding Goertzel Algorith" Aug. 1996, pp. 283-297 Signal Processing, Elsevier Science Publishers B.V. Amsterdam, NL vol. 52 No. 3.

Ogden Goertzel Alternative to the Fourier Transform: Jun. 1993 pp. 485-487 Electronics World; Reed Business Publishing, Sutton, Surrey, BG vol. 99, No. 9. 1687.

Medtrex Brochure "The O.R. Pro 300" 1 p. Sep. 1998.
Valleylab Brochure "Valleylab Electroshield Monitoring System" 2 pp. Nov., 1995.
Richard Wolf Medical Instruments Corp. Brochure, "Kleppinger Bipolar Forceps & Bipolar Generator" 3 pp. Jan. 1989.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.

* cited by examiner

*Primary Examiner*—Michael Peffley (57) ABSTRACT

A closed-loop control system has a user interface for allowing a user to select at least one pre-surgical parameter. The system also has a sensor module for continually sensing at least one of electrical and physical properties proximate a surgical site and generating at least one signal and a control module for continually receiving the selected parameter from the user interface and the at least one signal from the sensor module. The system processes the signal in accordance with the parameter using at least one of a microprocessor, computer algorithm and a mapping. The control module generates a corresponding control signal relating to the signal from the sensor module, and provides the control signal to the generator. The control module has number of loop control modules with a first loop control module providing a ratio of a real time parameter value to a desired parameter value. The real time parameter value is from the signal from the sensor module. The first loop control module modulates another loop control module based in part on the ratio for controlling the generator

25 Claims, 4 Drawing Sheets

METHOD AND SYSTEM FOR CONTROLLING OUTPUT OF RF MEDICAL GENERATOR

CROSS REFERENCE TO RELATED APPLICATIONS

This application is a continuation-in-part of U.S. application Ser. No. 10/073,761, filed on Feb. 11, 2002, by Wham et al., entitled "VESSEL SEALING SYSTEM" now which has issued as U.S. Pat. No.: 6,796,981, which is a continuation-in-part of U.S. Ser. No. 09/408,944, now U.S. Pat. No. 6,398,779, filed on Sep. 30, 1999 by Buysse et al., entitled "VESSEL SEALING SYSTEM", now U.S. Pat. No. 6,398,779 which claims the benefit of the priority date for provisional application No. 60/105,417, filed on Oct. 23, 1998, the entire contents of all of these applications are hereby incorporated by reference herein in their entirety.

BACKGROUND

The present invention is directed to electrosurgical surgery and, in particular, to a closed loop control system for an electrosurgical generator.

TECHNICAL FIELD

Electrosurgical generators are employed by surgeons in conjunction with an electrosurgical instrument to cut, coagulate, dessicate and/or seal patient tissue. High frequency electrical energy, e.g., radio frequency (RF) energy, is produced by the electrosurgical generator and applied to the tissue by the electrosurgical tool. Both monopolar and bipolar configurations are commonly used during electrosurgical procedures.

Electrosurgical techniques and instruments can be used to coagulate small diameter blood vessels or to seal large diameter vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. For the purposes herein, the term "cauterization" is defined as the use of heat to destroy tissue (also called "diathermy" or "electrodiathermy"). The term "coagulation" is defined as a process of desiccating tissue wherein the tissue cells are ruptured and dried. "Vessel sealing" is defined as the process of liquefying the collagen and elastin in the tissue so that it reforms into a fused mass with significantly-reduced demarcation between the opposing tissue structures (opposing walls of the lumen). Coagulation of small vessels is usually sufficient to permanently close them. Larger vessels or tissue need to be sealed to assure permanent closure.

In order to achieve one of the above desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

It is known that measuring the electrical impedance and change thereof across the tissue at the surgical site provides a good indication of the state of desiccation or drying of the tissue, e.g., as the tissue dries or looses moisture, the impedance across the tissue rises. This observation has been utilized in some electrosurgical generators to regulate the electrosurgical power based on a measurement of tissue impedance. For example, commonly owned U.S. Pat. No. 6,210,403 relates to a system and method for automatically measuring the tissue impedance and altering the output of the electrosurgical generator based on the measured impedance across the tissue. The entire contents of this patent is hereby incorporated by reference herein.

It has been determined that the particular waveform of electrosurgical energy can be tailored to enhance a desired surgical effect, e.g., cutting, coagulation, sealing, blend, etc. For example, the "cutting" mode typically entails generating an uninterrupted sinusoidal waveform in the frequency range of 100 kHz to 4 MHz with a crest factor in the range of 1.4 to 2.0. The "blend" mode typically entails generating an uninterrupted cut waveform with a duty cycle in the range of 25% to 75% and a crest factor in the range of 2.0 to 5.0. The "coagulate" mode typically entails generating an uninterrupted waveform with a duty cycle of approximately 10% or less and a crest factor in the range of 5.0 to 12.0. In order to effectively and consistently seal vessels or tissue, a pulse-like waveform is preferred. Energy may be supplied in a continuous fashion to seal vessels in tissue if the energy input/output is responsive to tissue hydration/volume through feedback control. Delivery of the electrosurgical energy in pulses allows the tissue to cool down and also allows some moisture to return to the tissue between pulses which are both known to enhance the sealing process.

It is further known to clamp or clip excess voltage output from the electrosurgical generator by the use of avalanche devices, such as diodes, zener diodes and transorbs, resulting in absorption and dissipation of excess energy in the form of heat.

Commonly owned U.S. Pat. No. 6,398,779 discloses a sensor which measures the initial tissue impedance with a calibrating pulse which, in turn, sets various electrical parameters based on a look-up table stored in a computer database. The transient pulse width associated with each pulse measured during activation is used to set the duty cycle and amplitude of the next pulse. Generation of electrosurgical power is automatically terminated based on a predetermined value of the tissue impedance across the tissue.

Thus a need exists to develop an electrosurgical generator having improved control circuitry and/or processing for providing continuous control of various electrical parameters (e.g., pulse frequency and intensity, voltage, current, power) of the electrosurgical generator based upon sensing information obtained from the surgical site relating to tissue impedance, changes in tissue impedance, tissue temperature, changes in tissue temperature, surgical intent (e.g., cutting, coagulating, sealing), tissue type, leakage current, applied voltage, applied current, tissue hydration levels, tissue compliance, and/or tissue optic transmission.

SUMMARY

A closed-loop control system is disclosed for use with an electrosurgical generator that generates electrosurgical energy. The closed loop control system includes a user interface for allowing a user to select at least one pre-surgical parameter, such as the type of surgical instrument operatively connected to the generator, the type of tissue and/or desired surgical effect. A sensor module is also included for continually sensing at least one of electrical and physical properties proximate a surgical site and generating at least one signal relating thereto. The closed loop control system also includes a control module for continually receiving the selected at least one pre-surgical parameter from the user interface and the at least one signal from the sensor module, and processing the at least one signal in accordance with the at least one pre-surgical parameter using a microprocessor, computer algorithm and/or a mapping (e.g., look-up table, continuous mapping and equivalent). The control module generates at least one corresponding control signal relating to the at least one signal from the sensor module, and relays the control signal to the electrosurgical generator for controlling the generator.

A method is also disclosed for performing an electrosurgical procedure at a surgical site on a patient. The method includes the steps of generating electrosurgical energy including at least one electrical pulse; applying the electrosurgical energy to the surgical site; continually sensing at least one of at least one electrical and physical property proximate the surgical site; and controlling the generating step for varying at least one parameter of the electrosurgical energy in accordance with the continually-sensed at least one property.

In another embodiment, a control system is provided, which includes a sensor module for sensing at least one property associated with a surgical site prior to a surgical procedure (pre-surgical), during the surgical procedure and/or after the surgical procedure (post-surgical). The sensor module generates at least one signal relating to the property back to the control module. A control module which is executable on a processor receives the at least one signal and processes the at least one signal utilizing a computer algorithm and/or a mapping and generates one or more control signals relating thereto. The control signal is then communicated to the electrosurgical generator for controlling the generator.

BRIEF DESCRIPTION OF THE DRAWINGS

Various embodiments will be described herein below with reference to the drawings wherein.

DETAILED DESCRIPTION

Figure 1:
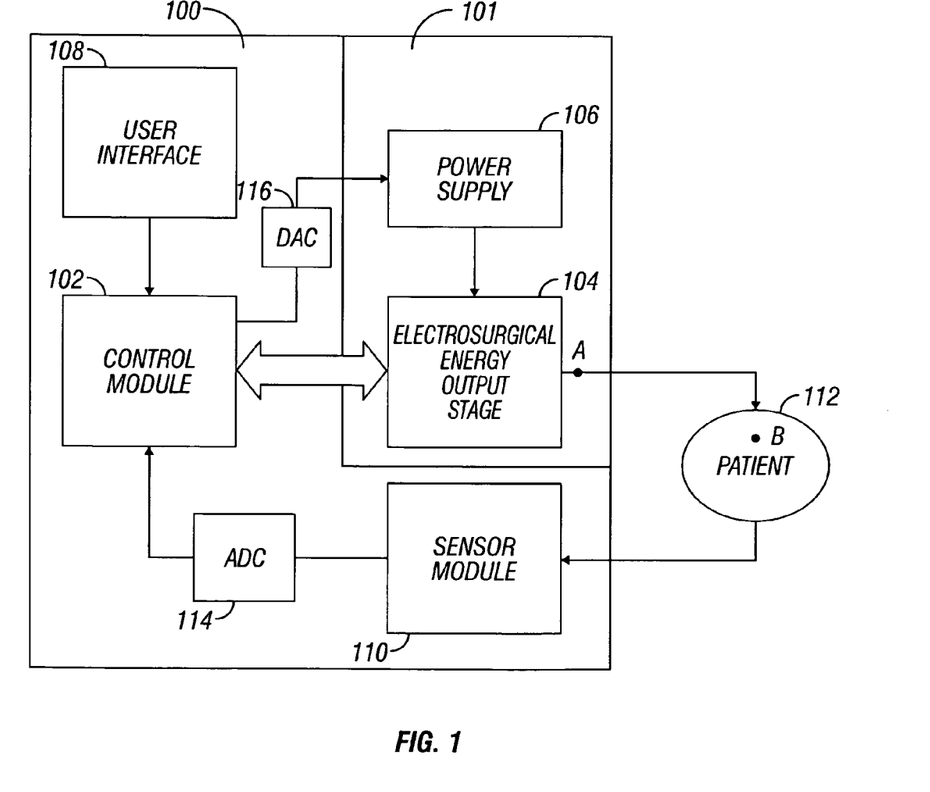
FIG. 1 is a schematic diagram of a closed-loop control system for use with an electrosurgical generator according to the present disclosure.

Reference should be made to the drawings where like reference numerals refer to similar elements throughout the various figures. Referring to FIG. 1, there is shown a schematic diagram of one embodiment of the presently disclosed closed loop control system 100 for use with an electrosurgical generator 101. Control system 100 includes a control module 102, user interface 108 and sensor module 110. The control module 102 is operatively connected to the electrosurgical generator 101. The electrosurgical generator 101 preferably includes electrosurgical energy output stage 104 and a power supply 106, where the output stage 104 receives power from the power supply 106 and delivers RF energy to a patient 112 via at least one electrode (not shown). As can be appreciated one or more electrodes may be used with the electrosurgical instrument for performing monopolar or bipolar surgery.

The sensor module 110 senses various electrical and physical parameters or properties at the operating site and communicates with the control module 102 to regulate the electrosurgical output from the output stage 104. It is envisioned that the sensor module 110 may be configured to measure or "sense" various electrical or electromechanical conditions at the operating site such as: tissue impedance, changes in tissue impedance, tissue temperature, changes in tissue temperature, leakage current, applied voltage and applied current. Preferably, the sensor module 110 measures one or more of these conditions continuously or in "real time" such that the control module 102 can continually modulate the electrosurgical output according to a specific purpose or desired surgical intent. More particularly, analog signals provided by the sensor module 110 are converted to digital signals via an analog-to-digital converter (ADC) 114, which in turn are provided to the control module 102.

The control module 102, thereafter, regulates the power supply 106 and/or the output stage 104 according to the information obtained from the sensor module 110. The user interface 108 is electrically connected to the control module 102 to allow the user to control various parameters of the electrosurgical energy output to the patient 114 during surgery to manually set, regulate and/or control one or more electrical parameters of the delivered RF energy, such as voltage, current, power, frequency, amplitude, and/or pulse parameters, e.g., pulse width, duty cycle, crest factor, and/or repetition rate depending upon a particular purpose or to change surgical intent.

The control module 102 includes at least one microprocessor capable of executing software instructions for processing data received by the user interface 108 and the sensor module 110 for outputting control signals to the output stage 104 and/or the power supply 106, accordingly. The software instructions executable by the control module are stored in an internal memory in the control module 102, an internal or external memory bank accessible by the control module 102 and/or an external memory, e.g., an external hard drive, floppy diskette, CD-ROM, etc. Control signals from the control module 102 to the electrosurgical generator 101 may be converted to analog signals by a digital-to-analog converter (DAC) 116.

The power supply 106 is preferably a high voltage DC power supply for producing electrosurgical current, e.g., radiofrequency (RF) current. Signals received from the control module 102 control the magnitude of the voltage and current output by the DC power supply. The output stage 104 receives the output current from the DC power supply and generates one or more pulses via a waveform generator (not shown). As can be appreciated, the pulse parameters, such as pulse width, duty cycle, crest factor and repetition rate are regulated in response to the signals received from the control module 102. Alternatively, the power supply 106 may be an AC power supply, and the output stage 104 may vary the waveform of the signal received from power supply 106 to achieve a desired waveform.

As mentioned above, the user interface 108 may be local to or remote from the control module 102. A user may enter data, such as the type of electrosurgical instrument being used, the type of electrosurgical procedure to be performed, and/or the tissue type upon which the electrosurgical procedure is being performed. It is envisioned that the closed loop control system 100, in particular the sensor module, may include one or more smart sensors which provide feedback to the surgeon relating to one or more of these physical parameters. Furthermore, the user may enter commands, such as a target effective voltage, current or power level to be maintained, or a target response, e.g., change in regulation of the power supply 106 and/or output stage 104, to changes in sensed values, such as an effective change in voltage, current and/or power level as a function of the changes. Preferably, the user may also enter commands for controlling electrical parameters of the RF energy, delivered by the electrosurgical generator 101, as described above. It is envisioned that default values are provided for the above target levels and target responses.

The sensor module 110 includes a plurality of sensors (not shown) strategically located for sensing various properties or conditions at or proximate points "A" and "B". Sensors positioned at or proximate point "A" (hereinafter referred to as at point "A") sense properties and/or parameters of electrosurgical output from output stage 104, and/or properties, parameters or conditions prior to surgical effect of the currently administered electrosurgical energy during the surgical procedure. For example, sensors positioned at point "A" may be provided with or attached proximate the generator 101.

Sensors positioned at or proximate point "B" (hereinafter referred to as at point "B") sense parameters, properties and/or conditions at or across the operating site prior to the surgical procedure and/or in response to surgical effect during the surgical procedure. Preferably, one or more of these sensors may be included with the electrosurgical instrument, (e.g., on one end effector or opposing end effectors) or attached proximate the operating site. For example, optical sensors, proximity sensors, temperature sensors may be used to detect certain tissue characteristics, and electrical sensors may be employed to sense other parameters of the tissue or operating effects. It is noteworthy that point "A" may be located proximate the surgical site "B" at a location where the signals outputted by the generator 101 are propagated before they are applied or approximately when they are applied to the surgical site "B".

The sensors are provided with leads or wireless means for transmitting information to the control module, where the information is provided directly to the control module 102, and/or provided to the control module 102 via the sensor module 110 and/or the ADC 114. The sensor module 110 may include means for receiving information from multiple sensors, and providing the information and the source of the information (e.g., the particular sensor providing the information) to the control module 102.

Figure 2:
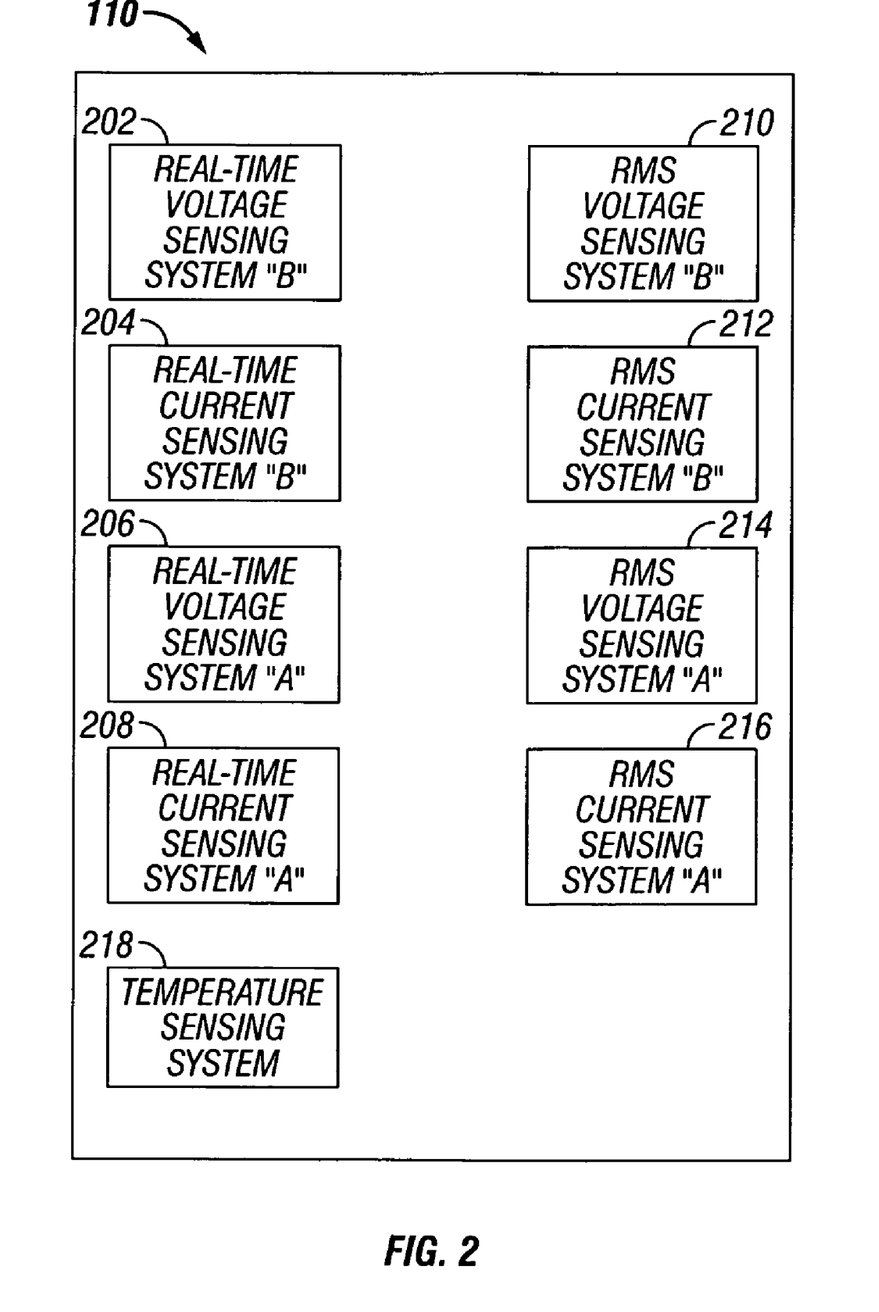
FIG. 2 is a schematic diagram of a sensor module for use with the closed-loop control system of FIG. 1.

With reference to FIG. 2, the inner-working components of the sensor module 110 are shown in greater detail. More particularly, the sensor module 110 preferably includes a real-time voltage sensing system 202 and a real-time current sensing system 204 for sensing real-time values for applied voltage and current at the surgical site "B". The sensor module 110 also preferably includes a real-time voltage sensing system 206 and a real-time current sensing system 208 for sensing real-time values of signals returned from the patent at a point "A". An RMS voltage sensing system 210 and an RMS current sensing system 212 are also included for sensing and deriving RMS values for applied voltage and current at the surgical site "B", and an RMS voltage sensing system 214 and an RMS current sensing system 216 are included for sensing and deriving RMS values of signals at point "A". A temperature sensing system 218 is preferably included for sensing tissue temperature at the surgical site "B". Real-time and RMS current and voltage sensing systems are known in the art. The sensor module 110 may further include sensors (not shown) for sensing voltage and current output by the generator.

The measured or sensed values are further processed, either by circuitry and/or a processor (not shown) in the sensor module 110 and/or by the control module 102, for deriving changes in sensed values and tissue impedance at the surgical site "B". Tissue impedance and changes in tissue impedance may be determined by measuring the voltage and/or current across the tissue and/or calculating changes thereof over time, and comparing the voltage and current values to known and/or desired values associated with various tissue types for use by the control system 100 to drive electrical output to achieve desired impedance and/or change in impedance values. As can be appreciated, these known and/or desired values, tissue types and ranges may be stored in an internal look-up table, "a continuous value map" or in an external searchable memory. Commonly owned U.S. Pat. No. 6,398,779, U.S. Pat. No. 6,203,541, U.S. Pat. No. 5,827,271 and U.S. application Ser. No 10,073,761 disclose methods for measuring tissue impedance, and are incorporated by reference herein in their entirety.

It is envisioned that deriving tissue impedance (or other physical and electrical parameters) from real-time value(s) provides the benefit of monitoring real-time tissue impedance and/or changes in tissue impedance. As the surgical procedure proceeds, it is believed that the tissue impedance fluctuates in response to removal and restoration of liquids from the tissue at the surgical site "B". As the control module 102 monitors the tissue impedance and changes in tissue impedance (or other physical and electrical parameters) the control module 102 regulates the power supply 106 and output stage 104 accordingly for achieving the desired and optimal electrosurgical effect.

Before beginning an electrosurgical procedure, an operator of the electrosurgical instrument enters information via the user interface 108. Information entered includes, for example, the type of electrosurgical instrument being used, the type of procedure being performed (i.e., desired surgical effect), the type of tissue, relevant patient information, and a control mode setting. The control mode setting determines the amount of or type of control that the control module 102 will provide. As mentioned above, one or more sensors (not shown) may also be included to automatically provide information to the control module 102 relating to tissue type, initial tissue thickness, initial tissue impedance, etc.

Exemplary modes include, but are not limited to, one or a combination of one or more of the following modes: a first mode wherein the control module 102 maintains a steady selected output power, current and/or voltage value at site "A"; a second mode wherein the control module 102 maintains a steady selected output power, current and/or voltage value at site "B"; a third mode wherein the control module 102 maintains a variable selected output power, current and/or voltage values at site "A" which is dependent upon (i.e., a function of) time value(s) and/or sensed parameter(s) or changes in sensed parameter(s) during the procedure; a fourth mode wherein the control module 102 maintains a variable selected output power, current and/or voltage values at site "B", which is dependent upon (i.e., a function of) time value(s) and/or sensed parameter(s) or changes in sensed parameter(s) during the procedure. Functions performed on the time value(s) and sensed properties(s) include operations such as calculations and/or look-up operations using a table or map stored by or accessible by the control module 102. The control module 102 processes the selected output power, current and voltage values, such as by performing calculations or table look up operations, to determine power control signal values and output control values.

It is also envisioned that, the control module 102 determines initial settings for control signals to the power supply 106 and the output stage 104 by using and/or processing operator-entered data or settings, performing calculations and/or accessing a look-up table stored by or accessible by the control module 102. Once the electrosurgical procedure begins, the sensors of sensor module 110 sense various physical and electrical properties and provide feedback to the control module 102 through the ADC 114 as needed. The control module 102 processes the feedback information in accordance with the pre selected mode, as well as any additional operator-entered commands entered during the procedure. The control module then sends control information to the power supply 106 and the output stage 104. It is contemplated that the generator 101 may be provided with override controls, to allow the operator to override the control signals provided by the control module 102, if needed, e.g., by entering override commands via the user interface 108.

Figure 3:
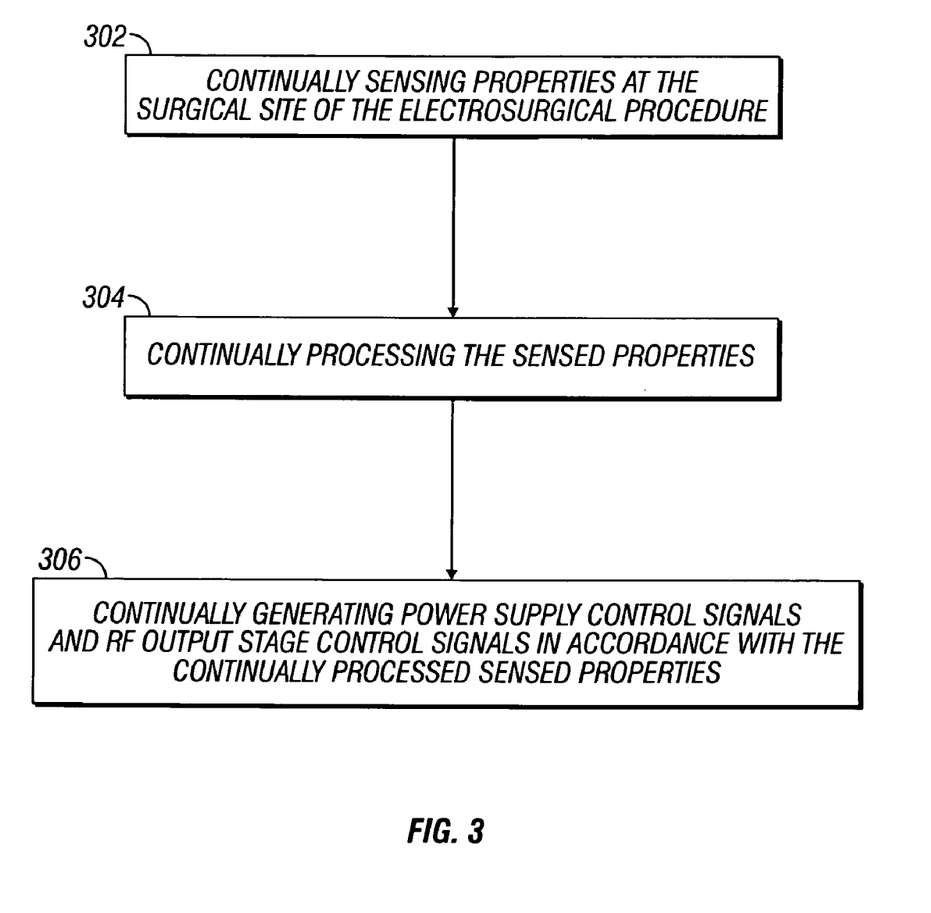
FIG. 3 is a flowchart illustrating a method of operation of the closed-loop control system according to the present disclosure.

FIG. 3 shows a flow chart illustrating a method for controlling operation of the closed loop control system 100 during an electrosurgical procedure in accordance with an embodiment of the present disclosure. At step 302, the method includes continually sensing various physical and electrical properties at the surgical site. At step 304, the sensed properties are continually processed. At step 306, power supply control signals are continually generated for controlling the magnitude of the signals output by the electrosurgical generator and output stage control signals are continually generated, for controlling pulse parameters of the output signals in accordance with the continually-processed sensed properties.

It is contemplated that the sensor module 110 further includes a proximity sensor for sensing (measuring) tissue thickness proximate the surgical site "B", and generating a tissue thickness value. An initial tissue thickness value may be provided to the control module 102 as a pre-surgical parameter. Sensed real time tissue thickness values and/or changes in tissue thickness values over time (Δ[difference] thickness/Δ[difference] time) may further be provided to the control module 102 during the surgical procedure, where the control module 102 modulates the electrical surgical output in accordance with the sensed real time tissue thickness values and/or changes in tissue thickness values over time.

It is further contemplated that the sensor module 110 further includes an additional sensor module (or the same sensor module 110 with additional capabilities) for sensing (measuring) tissue moisture (which is often indicative of tissue type) and generating a moisture content value and/or determining tissue type. It is envisioned that moisture content is determined from tissue compliance data or optical clarity. The additional sensor module may include an infrared or optical sensor for sensing (measuring) light or energy generated by a source, such as an infrared or other light source, which is transmitted through or reflected from the tissue, where the sensed value is indicative of tissue moisture content and/or tissue type of tissue proximate the surgical site "B". An initial tissue moisture content value and/or tissue type may be provided to the control module 102 as a pre-surgical parameter. Sensed real time moisture content values and/or changes in moisture content over time (Δ(difference) moisture content/Δ(difference) time) may further be provided to the control module 102 during the surgical procedure, where the control module 102 modulates the electrical surgical output in accordance with the sensed real time moisture content values and/or changes in moisture content values over time.

Accordingly, the present disclosure provides a closed loop control system 100 for providing continual control of the power supply 106 and the output stage 104 in response to "sensed" physical or electrical properties at the surgical site and/or proximate the output stage.

Figure 4:
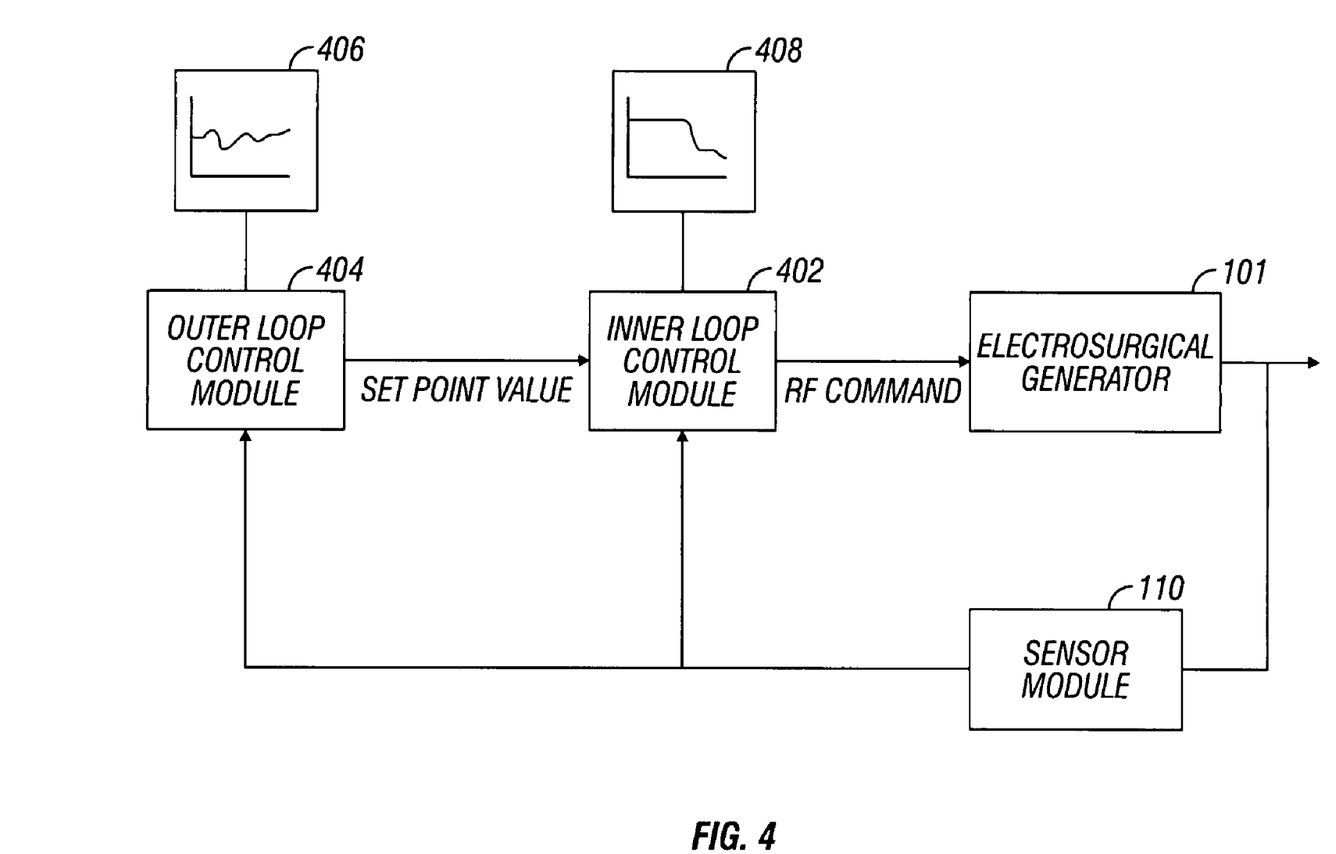
FIG. 4 is a block diagram of a dual loop control system in accordance with another embodiment of the invention.

In an additional embodiment according to the present disclosure and in particular reference to FIG. 4, the control module 102 is provided with two control loops, an inner loop controlled by inner loop control module 402 and an outer loop controlled by outer loop control module 404. Preferably, the inner and outer loop control modules 402, 404 are software modules executable by a processor of the control module 102. The inner and outer loop control modules 402, 404 both receive signals generated by sensor module 110.

The inner loop control module 402 controls the amount of current, voltage and/or power delivered to the tissue for controlling a variable, e.g., I, V or P, sensed at the tissue and/or calculated from sensed values, until a desired event occurs (a rapid dz/dt or impedance rise is achieved), e.g., an impedance value is reached preferably in the range of about 200 ohms to about 400 ohms. The control variable is controlled to change during the course of the seal cycle according to impedance value (or other sensed and/or derived values), as determined by generator limitations (power, current, voltage) and surgical limitations (maximum limits for application of energy to tissue).

The inner loop control module 402 continually receives real time sensed values, such as current I and voltage V, from the sensor module 110 and may perform calculations on the received values for deriving additional real time values, such as power P and impedance Z. A desired inner loop value for I, V, and/or P are obtained by accessing at least one stored inner mapping of continuous values 408, look-up table or equivalent, where preferably the inner mapping 408 is in accordance with a function of impedance. Preferably, the inner loop control module 402 consults the inner mapping 408 for obtaining the desired inner loop value for the impedance currently being sensed and derived.

An algorithm is used to compare the real time value of I, V and/or P to the respective desired inner loop value and output an RF command to the electrosurgical generator 101 accordingly for achieving the desired inner loop value without exceeding the desired inner loop value, e.g., the RF command raises the target current, voltage and/or power output by the electrosurgical generator 101 when the real time value for I, V and/or P is lower than the respective desired inner loop value for I, V and/or P, and vice versa. It is contemplated that the RF command controls waveform parameters of electrosurgical energy output by the electrosurgical generator 101, including current, power, voltage, duty cycle, frequency, waveshape, etc. It is further contemplated that the inner loop is used without the outer loop for achieving the desired tissue effect.

The outer loop control module 404, layered over the inner loop control module 402, provides additional control of a variable for reaching a desired output value or effect. For example, control of the variable may monitor/regulate the rate of change of impedance of the tissue (sensed and calculated). In different embodiments, the variables controlled may include temperature, rate of change of temperature, and/or the energy input to the tissue. Outer loop control module 404 continually receives sensed values, such as I, V and temperature T from the sensor module 110 at a time "t" and performs calculations on the sensed values and preferably stored values for deriving values such as rate of change of impedance and/or rate of change in temperature. For example, the value for change in impedance (dz/dt) is obtained in accordance with:

$$dz/dt = (Z - Z\_OLD)/(t - t\_OLD); \quad (1)$$

Z_OLD=Z;

where Z is the impedance in accordance with values measured at time t; and

Z_OLD is the stored impedance in accordance with values measured at a previous time interval at time t_OLD An outer loop desired value for the control variable is obtained by accessing a stored outer mapping of continuous values 406, or alternatively a table or equivalent. The desired rate of change according to outer mapping 406 may be steady, or may depend on the stage of the seal cycle and change over time. The tissue is in a dynamic state during the seal procedure, and the outer loop monitors the rate of change throughout the procedure to determine the degree to which the desired rate of change is being achieved. When the control variable is temperature, a temperature map may be used for outer mapping 406 in which desired temperature is plotted versus time. When the control variable is rate of change in temperature, a rate of change in temperature map may be used for outer mapping 406 in which desired temperature is plotted versus time. Energy may be applied in a similar fashion, where an energy function can be calculated using equations derived for specific tissue types or using sensed values.

An algorithm is used to compare the real time sensed/calculated value of rate of change of impedance, temperature, rate of change of temperature and/or energy at time "t" to the respective desired outer value at time "t" obtained from the outer mapping 406 for determining if the desired outer value is met, and if not, for determining the ratio of the difference between the real time value and the desired outer value to the desired outer value. If the desired outer value is not being met, the outer loop module 406 generates a set point value which is provided to the inner loop module 402. The set point value is raised when the real time value for rate of change of impedance, temperature and/or rate of change of temperature is lower than the respective desired outer value for rate of change of impedance, temperature and/or rate of change of temperature, and vice versa.

The set point value is preferably a ratio signal for altering the inner mapping 408 by raising or lowering a plotted curve of the inner mapping 408 along the y-axis. Preferably, the ratio signal is a proportional integral derivative (PID) control signal, as is known in the art. The inner loop control module 402 responds instantaneously by accessing the altered inner mapping 408 for obtaining a desired inner value from the outer loop, comparing the real time value of the control variable, generating an RF command for achieving the desired inner value without exceeding the desired inner value, and outputting the RF command accordingly to the electrosurgical generator 101 for controlling voltage, current and/or power needed for achieving a desired tissue effect.

Preferably the outer loop control module 404 uses the real time value of rate of change of impedance, temperature, rate of change of temperature, and/or total energy delivered to determine if a desired outer value has been reached which indicates completion of a seal. Upon determination of seal completion, a stop signal is generated for stopping the sealing process. Otherwise, the outer loop continues to monitor, receive and process sensed values from the senor module 110.

Control of I, V and/or P by the inner loop control module 402 improves system stability and control capabilities in low impedance ranges, e.g., 0–20 ohms, which are critical for seal initiation, particularly by avoiding a low-end impedance break point which induces oscillation and lack of system control. The outer loop control enhances the control module's ability to control sealing in accordance with desired trends or events, to change seal intensity by changing the rate of change of impedance, and to enhance uniform sealing of tissue, i.e., normalize tissue in terms of variability, including tissue hydration, volume and composition. With feedback control and continuous sensing of the tissue's condition, there is not a need to switch control variables (i.e., low/high end break points), which improves system stability as explained above.

It is contemplated that the control module 102 controls a module for producing resistive heat for regulating heat applied to the tissue for achieving the desired tissue effect instead of or in addition to controlling the electrosurgical output stage 104 and/or the power supply 106. The control module 102 responds to sensed tissue temperature or other sensed properties indicative of tissue temperature, accesses at least one mapping, data table or equivalent using the sensed values for obtaining desired output current or resistivity values, and outputs a command signal for controlling output heat resistivity. Preferably, the module for producing resistive heat includes a current source and/or a variable resistor which are responsive to the command signal for outputting a desired current or providing a desired resistance, respectively.

It is envisioned that in another embodiment of the invention the control system includes a sensor module for sensing at least one property associated with a surgical site during at least one of a pre-surgical time prior to a surgical procedure, the surgical procedure and a post-surgical time following the surgical procedure for generating at least one signal relating thereto; and a control module executable on a processor for receiving said at least one signal and processing said at least one signals using at least one of a computer algorithm and a mapping and generating at least one control signal in accordance with the processing, and providing the at least one control signal to the electrosurgical generator for controlling the generator. Preferably, the processing includes determining tissue type of tissue proximate the surgical site.

In an additional preferred embodiment, the sensor module 110 (or an additional sensor module (not shown)) senses at least one property as a pre-surgical condition, as a concurrent surgical condition and/or as a post-surgical condition. Preferably, the sensor module 110 senses at least two surgical conditions (or changes in surgical conditions over time) selected from pre-surgical, concurrent surgical and post-surgical conditions. Pre-surgical conditions include: degree of opaqueness of tissue proximate the surgical site; moisture content level of the tissue; and/or thickness of the tissue. Concurrent conditions include: degree of opaqueness of the tissue proximate the surgical site; moisture content level of the tissue; thickness of the tissue; temperature of the tissue; impedance of the tissue; current across the tissue; voltage across the tissue; power across the tissue; changes in degree of opaqueness of the tissue; changes in moisture content level of the tissue; changes in thickness of the tissue; changes in temperature of the tissue; changes in impedance of the tissue; changes in current across the tissue; changes in voltage across the tissue; and changes in power across the tissue. The post-surgical conditions include: degree of opaqueness of tissues proximate the surgical site; moisture content level of the tissue; thickness of the tissue: temperature of the tissue; and impedance of the tissue.

Preferably, at least one property sensed during the post-surgical condition is indicative of the quality of a tissue seal formed during the surgical procedure. In a preferred embodiment the sensor module 110 includes a light detector for detecting light generated by a light source and transmitted through (or reflected from) the tissue proximate the surgical site. A proximity sensor having sensing elements placed at opposite surfaces of the tissue may also be included for sensing the distance between the elements which is indicative of the tissue thickness.

Although this disclosure has been described with respect to preferred embodiments, it will be readily apparent to those having ordinary skill in the art to which it appertains that changes and modifications may be made thereto without departing from the spirit or scope of the disclosure. For example, it is contemplated that the control module 102 may include circuitry and other hardware, rather than, or in combination with, programmable instructions executed by a microprocessor for processing the sensed values and determining the control signals to be sent to the power supply 106 and the output stage 104.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

What is claimed is:

1. A closed-loop control system for use with an electrosurgical generator that generates electrosurgical energy including at least one pulse, said closed loop control system comprising:
   a user interface which allows a user to select at least one pre-surgical parameter, said at least one pre-surgical parameter including at least one of a type of surgical instrument operatively connected to the generator, type of tissue and desired surgical effect;
   a sensor module which continually senses at least one of electrical and physical properties proximate a surgical site and generating at least one signal relating thereto; and
   a control module which continually receives said selected at least one pre-surgical parameter from said user interface and said at least one signal from said sensor module, and processing said at least one signal in accordance with the at least one pre-surgical parameter using at least one of a microprocessor, computer algorithm and a mapping, said control module generating at least one corresponding control signal relating to said at least one signal from said sensor module, and providing the at least one control signal to the electrosurgical generator for controlling the generator;
   wherein said control module comprises a plurality of loop control modules with at least a first loop control module of said plurality of loop control modules providing a ratio between a real time parameter value and a desired parameter value;
   said real time parameter value being from said at least one signal from said sensor module, and wherein said first loop control modules modulates another of said plurality of loop control modules based in part on said ratio to control the generator.

2. The closed-loop control system according to claim 1, wherein said user interface includes at least one additional sensor which automatically selects a pre-surgical parameter of the at least one pre-surgical parameter.

3. The closed-loop control system according to claim 1, wherein said at least one control signal controls said generator to adjust at least one parameter of the generated electrosurgical energy.

4. The closed-loop control system according to claim 3, wherein said at least one control signal is capable of controlling said generator to adjust voltage, current, power, pulse width, frequency, amplitude, crest factor, duty cycle, repetition rate, and wave shape of the electrosurgical energy.

5. The closed-loop control system according to claim 1, wherein the generator includes a power source, and wherein the at least one control signal includes a power control signal for controlling the power source for adjusting a magnitude of an electrical characteristic of individual pulses of at least one pulse.

6. The closed-loop control system according to claim 1, wherein the at least one control signal adjusts wave shape parameters of individual pulses of the at least one pulse.

7. The electrosurgical generator according to claim 1, wherein the at least one control signal controls at least one of repetition rate and duty cycle of the at least one pulse.

8. The closed-loop control system according to claim 1, wherein the sensor module includes at least one of a voltage sensor, a current sensor, a temperature sensor, an RMS voltage sensor, an RMS current sensor and a leakage current sensor, and the microprocessor processes signals output by the RMS voltage sensor, the RMS current sensor and the leakage current sensor for deriving respective corresponding values for RMS voltage, RMS current and leakage current.

9. The closed-loop control system according to claim 1, wherein the sensor module is capable of sensing voltage, current, temperature, RMS voltage, RMS current and leakage current, and the microprocessor processes signals output by the RMS voltage sensor, the RMS current sensor and the leakage current sensor for deriving respective corresponding values for RMS voltage, RMS current and leakage current.

10. The closed-loop control system according to claim 1, wherein the sensor module further includes a voltage sensor for sensing voltage delivered to or returned from the surgical site.

11. The closed-loop control system according to claim 1, wherein the sensor module further includes a current sensor which senses current delivered to or returned from the surgical site.

12. The closed-loop control system according to claim 1, wherein the sensor module further includes means for measuring electrical impedance.

13. The closed-loop control system according to claim 1, wherein the closed-loop control system further includes means for measuring changes in sensed temperature.

14. The closed-loop control system according to claim 1, wherein the closed-loop control system further includes means for processing information from the sensor module for determining electrical impedance at the surgical site.

15. The closed-loop control system according to claim 14, wherein the processing means measures changes in the electrical impedance.

16. The closed-loop control system according to claim 1, wherein the user interface further allows a user to enter commands for processing by the control module for controlling the electrosurgical generator to generate the energy having at least one of a target electrical parameter including at least one of voltage, current, power, frequency and amplitude; pulse parameter including at least one of pulse width, duty cycle, crest factor and repetition rate; and electrical parameter change in response to changes in at least one of sensed physical and electrical properties.

17. A system for electrosurgically sealing tissue, comprising an electrosurgical generator comprising an RF energy source and a controller for controlling the operation of an electrosurgical generator, said electrosurgical generator having an output for coupling to a surgical instrument comprising electrodes for coupling RF energy generated by said electrosurgical generator to tissue to be sealed; said controller being operable for causing said electrosurgical generator to apply an initial pulse of RF energy to the tissue and for measuring a value of an electric characteristic of the tissue in response to the applied initial pulse, said controller being responsive to the measured electrical characteristic for determining an initial set of pulse parameters for a subsequent pulse and for then varying the pulse parameters of individual pulses of further subsequent RF energy pulses in accordance with a change in the electrical characteristic of the tissue;
wherein the controller is further operable for measuring an electrical and a physical characteristic of the tissue in response to the individual pulses and for then varying the pulse parameters of subsequent individual pulses in accordance with the electrical and physical characteristics of the tissue.

18. A control system to control an electrosurgical generator that generates electrosurgical energy including at least one pulse, the control system comprising:
a sensor module which senses at least one property associated with a surgical site as one of a pre-surgical condition, concurrent surgical condition or a post-surgical condition and generating at least one signal relating thereto; and
a control module executable on a processor which receives said at least one signal from said sensor module and processing said at least one signal using at least one of a computer algorithm and a mapping and generating at least one control signal in accordance with the processing, said control module providing the at least one control signal to the electrosurgical generator and being configured to control the generator, wherein said control module comprises a plurality of loop control modules with at least a first loop control module of said plurality of loop control modules providing a ratio between a real time parameter value and a desired parameter value;
said real time parameter value being from said at least one signal from said sensor module, and wherein said first loop control modules modulates another of said plurality of loop control modules based in part on said ratio to control the generator.

19. The control system according to claim 18, wherein the sensor module senses the at least one property during at least two of the pre-surgical condition, the concurrent surgical condition and the post-surgical condition.

20. The control system according to claim 18, wherein the at least one property sensed during the pre-surgical condition includes at least one of: degree of opaqueness of tissue proximate the surgical site; moisture content level of tissue; and thickness of tissue.

21. The control system according to claim 18, wherein the processing includes determining type of tissue.

22. The control system according to claim 18, wherein the at least one property sensed during the concurrent surgical condition includes at least one of:
degree of opaqueness of tissue proximate the surgical site;
moisture content level of tissue;
thickness of tissue;
temperature of tissue, impedance across tissue;
current across tissue;
voltage across tissue;
power across tissue;
changes in degree of opaqueness of tissue;
changes in moisture content level of tissue;
changes in thickness of tissue;
changes in temperature of tissue;
changes in impedance across tissue;
changes in current across tissue;
changes in voltage across tissue; and
changes in power across tissue.

23. The control system according to claim 18, wherein the at least one property sensed during the post-surgical condition includes at least one of: degree of opaqueness of tissue proximate the surgical site; moisture content level of tissue; thickness of tissue; temperature of tissue; and impedance across tissue.

24. The control system according to claim 18, wherein the control module determines quality of a tissue seal formed during the surgical procedure in accordance with the processing of the at least one signal, wherein the processed at least one signal relates to at least one of: degree of opaqueness of tissue proximate the surgical site; moisture content level of tissue; thickness of tissue; temperature of tissue; impedance across tissue, rate of change of temperature of tissue, rate of change of impedance across tissue, and total energy delivered to tissue.

25. The control system according to claim 18, wherein the sensor module includes a light detector being configured to detect light generated by a light source and transmitted through tissue proximate the surgical site, and a proximity sensor having sensing elements, said sensing elements being between a first location and a second location of tissue, said first location and said second location being separated by a distance, said sensing elements being configured to sense said distance between said sensing elements.

* * * * *

UNITED STATES PATENT AND TRADEMARK OFFICE
CERTIFICATE OF CORRECTION

PATENT NO. : 7,137,980 B2 Page 1 of 1
APPLICATION NO. : 10/427832
DATED : November 21, 2006
INVENTOR(S) : Steven B. Buysse et al.

It is certified that error appears in the above-identified patent and that said Letters Patent is hereby corrected as shown below:

Title Page, Item (75) Inventors: Add the Following Inventor.

-- Jeremy S. James, Westminster, CO --.

Signed and Sealed this

Thirtieth Day of December, 2008

JON W. DUDAS
*Director of the United States Patent and Trademark Office*